(12) United States Patent
Tyler

(10) Patent No.: US 7,377,666 B1
(45) Date of Patent: May 27, 2008

(54) ILLUMINATED EAR PROTECTOR

(76) Inventor: Paul Tyler, 11401 Golf Links Rd., Oakland, CA (US) 94605

( * ) Notice: Subject to any disclaimer, the term of this patent is extended or adjusted under 35 U.S.C. 154(b) by 0 days.

(21) Appl. No.: 11/696,686

(22) Filed: Apr. 4, 2007

(51) Int. Cl.
*F21V 21/084* (2006.01)
*H04R 1/10* (2006.01)
*H04R 31/00* (2006.01)

(52) U.S. Cl. .................. 362/105; 362/253; 362/86; 362/300; 362/311

(58) Field of Classification Search ............ 362/103, 362/105, 106, 234, 253, 86, 800, 296, 300, 362/310, 311, 363; 2/209, 423; 381/74, 381/370, 371
See application file for complete search history.

(56) References Cited

U.S. PATENT DOCUMENTS

| | | | | |
|---|---|---|---|---|
| 4,969,069 A | * | 11/1990 | Eichost | 362/105 |
| 5,751,825 A | * | 5/1998 | Myers et al. | 381/118 |
| 6,081,604 A | * | 6/2000 | Hikichi et al. | 381/371 |
| 6,606,506 B1 | * | 8/2003 | Jones | 455/556.1 |
| 6,918,678 B2 | * | 7/2005 | McClanahan | 362/105 |
| 7,020,902 B1 | * | 4/2006 | Tyler | 2/209 |
| 7,114,823 B2 | * | 10/2006 | McCullough et al. | 362/105 |

\* cited by examiner

*Primary Examiner*—Jacob Y. Choi
(74) *Attorney, Agent, or Firm*—Howard E. Lebowitz; Foothill Law Group, LLP

(57) ABSTRACT

An illuminated ear protector, comprising a pair of ear covers, each ear cover comprising a translucent rigid shell having an open end and a closed end, a circuit board attached within the rigid shell comprising at least one battery connector thereon, at least one and preferably two light emitting diode lights electrically connected to the circuit board, a switch connected to the circuit board controlling the at least one light emitting diode light, a first reflector located at the open end and oriented such that substantially all light from the at least one light emitting diode light is directed towards the closed end, a plate attached to the open end which supports the reflector, a peripheral sealing ring for contacting one of the ears and cushioning the ear cover there against which is attached to an opposite side of the plate from the reflector, and a headband attached to each of the ear covers which extends over the head of the user and secures each of the ear covers over one of the ears of the user.

11 Claims, 3 Drawing Sheets

ILLUMINATED EAR PROTECTOR

BACKGROUND OF THE INVENTION

1. Field of the Invention

The invention relates to ear protectors, particularly internally illuminated ear protectors which make the wearer visible to others in the dark and which provide protection to the ears in noisy environments. The illumination can also provide an internal heating source.

2. Description of the Prior Art

Ear protectors, also known as ear muffs, are known for several purposes, including insulation from cold and insulation from loud noises. The ears are particularly sensitive to both cold temperatures and noisy environments.

Typically, earmuffs for cold insulation comprise a pair of earmuff elements each in the form of a large, thick, insulated disk sized to cover the ear. These earmuff elements are rather stiff constructs, and they are usually interconnected by an arcuate strip of metal or plastic that is stiff yet resilient enough so that the earmuff elements may be positioned over the ears or held in position with the spring-like action of the band member which arches over and is supported by the top of the wearer's head. Earmuffs work by attempting to insulate the ears and prevent them from losing heat. However, in extreme cold and when spending extended period of time outdoors, conventional earmuffs may be insufficient to keep the ears warm.

The ears are also vulnerable to damage in noisy environments. Specifically designed ear guards are often employed to protect the hearing those engaged in certain occupations that subject them to dangerously high noise levels for extended periods of time. In particular, airport crew and construction workers often wear noise attenuating ear guards to lower the sound levels they are subjected to. Typically, however, these ear guards do not provide any significant protection from cold temperatures.

It should be noted that many of these same professions that subject workers to prolonged exposure to cold and/or noise also subject the worker to the hazard of vehicles and heavy objects colliding with the worker. Accordingly, in many of these professions, improving the visibility of the worker greatly increases safety and helps prevent accidents.

U.S. Pat. No. 6,511,202 to Henry, which is hereby incorporated herein by reference, discloses a high-low light-emitting diode glow-in-the-dark flashlight. The flashlight includes an end cap assembly that snaps onto the top of a 9-volt battery. The battery functions as both a power source and a handle. The flashlight is very light and compact.

Accordingly, there is a need for an ear protector that reliably protects the ears of a wearer from loud noises in the environment, while increasing the visibility of the wearer to enhance the safety thereof.

There is also a need for an ear protector that reliably protects the ears of a wearer from loud noises in the environment, while increasing the visibility of the wearer to enhance the safety thereof and additionally providing an internal heat source.

SUMMARY OF THE INVENTION

It is an object of the invention to provide ear protectors which protect the ears of a wearer against loud noises while also improving the safety of the wearer by providing internal illumination to make the ear protectors highly visible in the dark by making the protectors glow with a diffused light.

It is another optional object of the invention to provide a heating source which will radiate heat to the ears of the wearer in addition to the insulating value.

The invention is an illuminated ear protector, for use by a user having a head and ears, comprising a pair of ear covers, each ear cover comprising a translucent rigid shell having an open end and a closed end, a circuit board attached within the rigid shell comprising at least one battery connector thereon, at least one and preferably two light emitting diode lights electrically connected to the circuit board, a switch connected to the circuit board controlling the at least one light emitting diode light, a first reflector located at the open end and oriented such that substantially all light from the at least one light emitting diode light is directed towards the closed end, a plate attached to the open end which supports the reflector, a peripheral sealing ring for contacting one of the ears and cushioning the ear cover there against which is attached to an opposite side of the plate from the reflector, and a headband attached to each of the ear covers which extends over the head of the user and secures each of the ear covers over one of the ears of the user. Each ear cover preferably also comprises a battery holder attached to the rigid shell and partially extending through the rigid shell such that a battery inserted therein will mate with the at least one battery connector on the circuit board. To operate the invention a battery is inserted in the battery holder.

Light emitting diodes were chosen for the lights because it was found that an ordinary small incandescent flashlight bulb generates too much heat and makes the protectors uncomfortable to wear, even in cold weather. It is possible to provide some heating effect, however, by using two different LED lights, a first LED that is less efficient and generates more heat than a second LED which is a normal efficient LED. In this case the switch is a three position switch wherein in a first position only the first light is illuminated, in a second position neither light is illuminated, and in a third position only the second light is illuminated.

In the case where internal heating is not desired, two ordinary LEDs are used and the switch can be either a two position switch (ON-OFF) or a three position switch (HIGH INTENSITY-OFF-LOW INTENSITY).

Each ear cover also preferably includes a sheet of translucent foam insulation shaped to fit in the closed end, whereby the light emitted from the closed end is diffused and sound penetration to the user's ear is reduced. The ear cover further comprises a second foam sheet attached to the plate on a side opposite to the first reflector, whereby additional sound protection is provided to the user.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

These and other features, aspects and advantages of the present invention will become better understood with regard to the following description, appended claims and accompanying drawings, where:

DESCRIPTION

Figure 1:
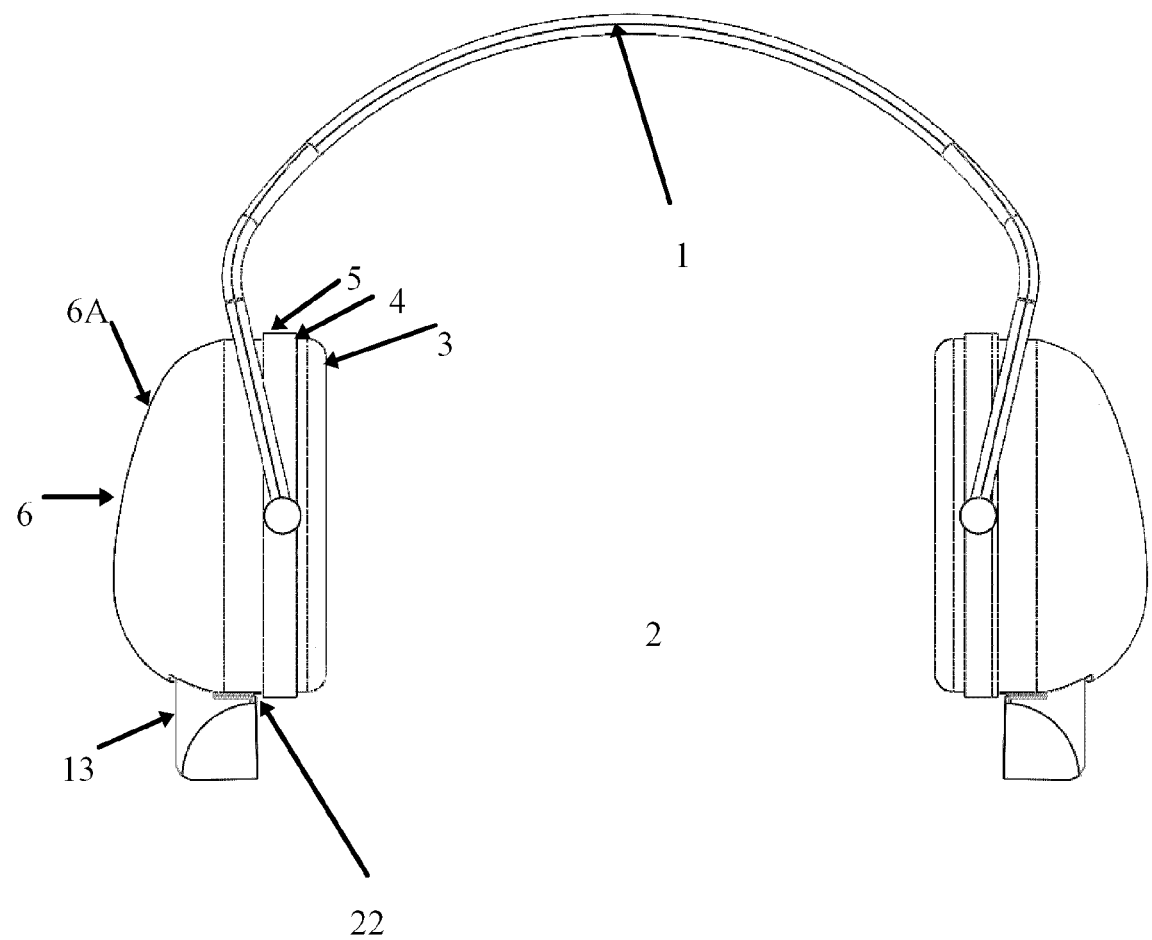
FIG. 1 is a front elevational view, illustrating the ear guards of the present invention.

FIG. 1 illustrates the illuminated ear protectors 2 according to a preferred embodiment of the invention, comprising two ear covers and headband 1. The ear covers each have a translucent rigid shell 6A having a closed end 6 and an open end 22 (better seen in FIG. 3), plate 5, and foam sheet 4, and foam peripheral sealing ring 5. The headband is attached such that the peripheral sealing rings on each ear cover are oriented towards each other. The headband has an adjustment mechanism which allows its length to be adjusted to accommodate different size users.

Figure 2:
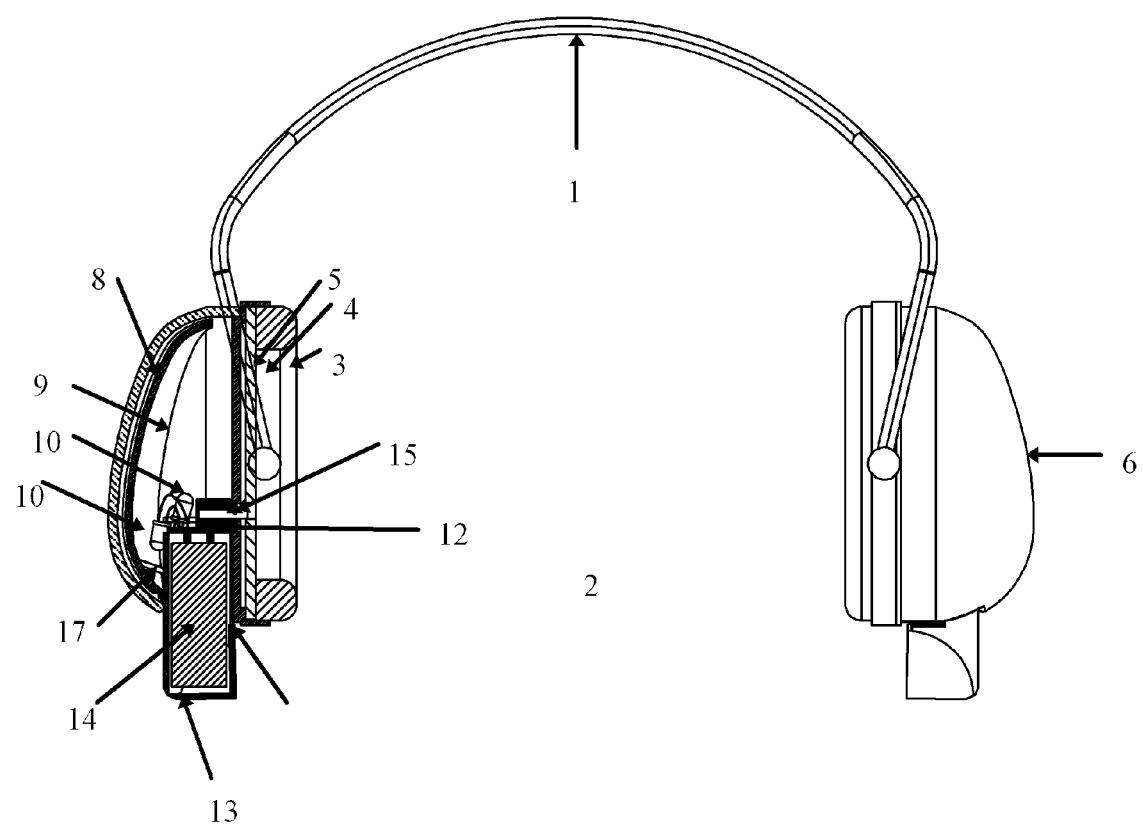
FIG. 2 is a front elevational view, with a portion of one of the ear cover assemblies broken away to show internal details thereof.
Figure 3:
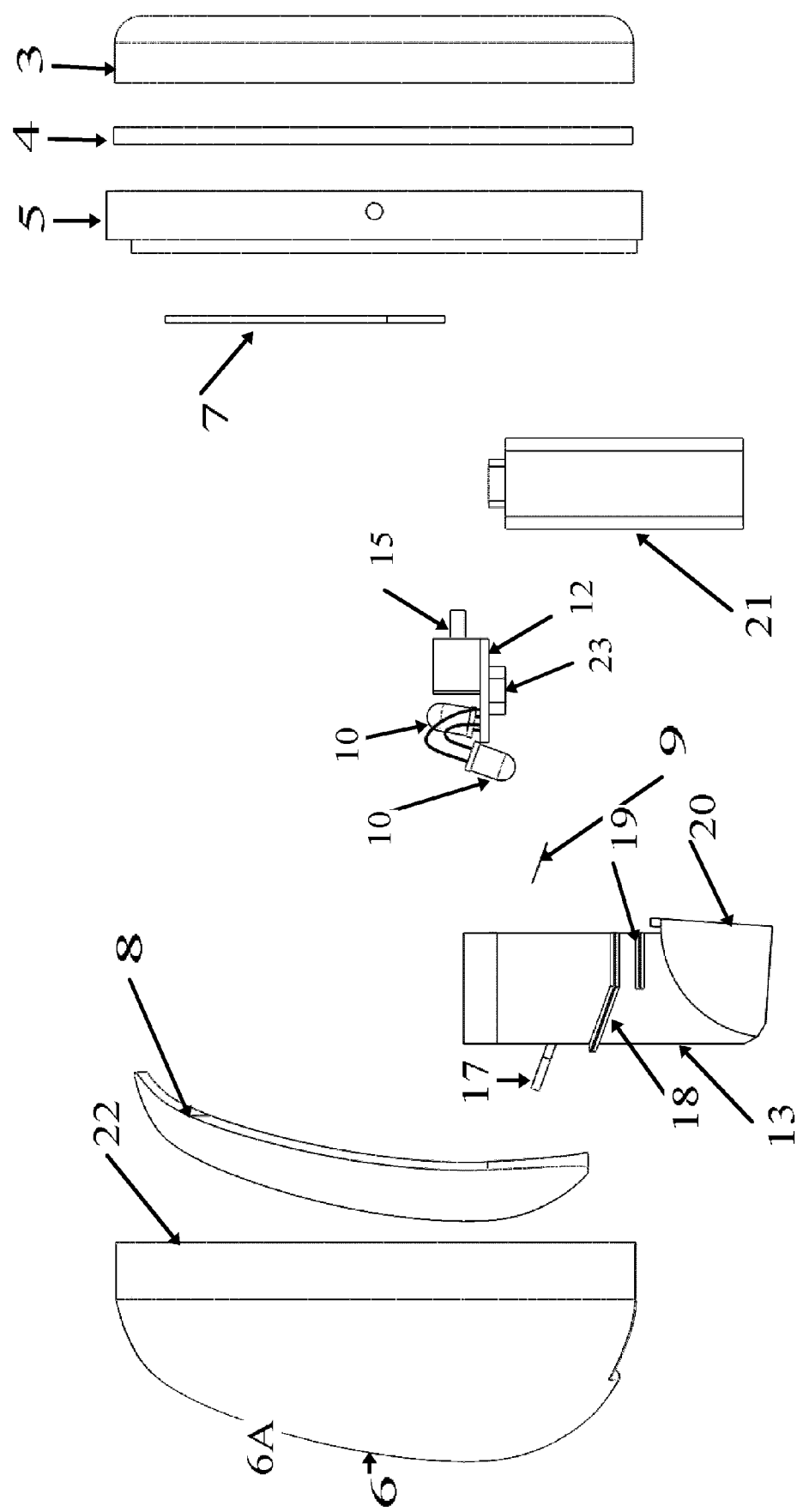
FIG. 3 is an exploded view of one of the ear covers.

FIG. 2 and FIG. 3 (an exploded view) illustrates the internal structure of an ear cover. Each ear cover has a translucent rigid shell 6A comprising a closed end 6 and an open end 22. There is a translucent foam diffuser sheet 8 (FIG. 3) shaped to fit snugly on the closed end. The diffuser diffuses the light generated within shell so that the translucent rigid shell appears uniformly illuminated. The diffuser also provides sound and thermal insulation value. The rigid shell is preferably hard translucent plastic, and the diffuser is preferably open cell translucent foam.

A printed circuit board 12 is attached within the rigid shell comprising at least one battery connector 23 thereon, at least one and preferably two light emitting diode lights 10 electrically connected to the circuit board, a switch 15 connected to the circuit board controlling the at least one light emitting diode light. A battery holder 13 extends through the rigid shell such that a battery inserted therein will mate with the at least one battery connector on the circuit board. A battery 21 is inserted in the battery holder with its at least one connector engaging with the at least one connector on the circuit board. The battery holder is preferably made from a hard plastic. The battery holder has a door 20 through which a battery may be inserted or removed. Preferably the battery is a standard 9 volt alkaline battery. The battery holder has brackets 18 and 19 for securing it in an opening in the rigid shell. The battery holder has a platform 17 for mounting a small mirror 9.

Light emitting diodes were chosen for the lights because it was found that an ordinary small incandescent flashlight bulb generates too much heat and makes the protectors uncomfortable to wear, even in cold weather. It is possible to provide some heating effect, however, by using two different types LED lights, a first LED that is less efficient and therefore generates more heat than a second LED which is a normal efficient LED. In this case the switch is a three position switch wherein in a first position only the first light is illuminated, in a second position neither light is illuminated, and in a third position only the second light is illuminated.

In the case where internal heating is not desired, two ordinary LEDs are used and the switch can be either a two position switch (ON-OFF) or a three position switch (HIGH INTENSITY-OFF-LOW INTENSITY).

A plate 5 is provided, which is press fit and cemented into the rigid shell and holds the ear cover together. Onto one side of the plate is cemented a reflector 7, which directs substantially all of the light generated by the LEDs out through the translucent rigid shell. The optional small mirror 9 mounted on the platform 17 of the battery holder directs light to the reflector 7, creating a more uniform lighting. It is also possible to use encapsulated LEDs which have a built in reflector which can be focused to shine on the reflector 7 without need for a small mirror 9. On the opposite side of the plate from the reflector is attached a second foam sheet 14 providing sound and thermal insulation value. It is preferably closed shell foam. Finally, cemented to the plate is a peripheral sealing ring 3 for contacting one of the ears and cushioning the ear cover there against. Preferably the sealing ring is made of rubber fabric or fabric covered rubber.

Note that the switch 15 extends through the plate and the second foam sheet so the lights can be adjusted through open side of the ear cover (see particularly FIG. 2).

The ear protectors are used by adjusting the LEDs as desired with the switch 15, placing the headband on the users head with the ear covers over the ears.

Although the present invention has been described in considerable detail with reference to certain preferred versions thereof, other versions are possible. Therefore the spirit and scope of the appended claims should not be limited by the preferred versions herein.

What is claimed is:

1. An illuminated ear protector, for use by a user having a head and ears, comprising:
   a pair of ear covers, each ear cover comprising
      a translucent rigid shell having an open end and a closed end,
      a circuit board attached within the rigid shell comprising at least one battery connector thereon,
      at least one light emitting diode light electrically connected to the circuit board,
      a switch connected to the circuit board controlling the at least one light emitting diode light,
      a first reflector located at the open end and oriented such that substantially all light from the at least one light emitting diode light is directed towards the closed end,
      a plate attached to the open end which supports the reflector,
      a peripheral sealing ring for contacting one of the ears and cushioning the ear cover there against which is attached to an opposite side of the plate from the reflector, and
   a headband attached to each of the ear covers which extends over the head of the user and secures each of the ear covers over one of the ears of the user.

2. The illuminated ear protector as recited in claim 1, wherein the at least one light emitting diode light comprises two light emitting diode lights.

3. The illuminated ear protector as recited in claim 1, further comprising a battery holder attached to the rigid shell and partially extending through the rigid shell such that a battery inserted therein will mate with the at least one battery connector on the circuit board.

4. The illuminated ear protector as recited in claim 3, further comprising a battery door on the battery holder, whereby a battery placed in the battery holder will be held in place by the battery door.

5. The illuminated ear protector recited in claim 2, wherein the two light emitting diode lights comprise a first light having low heat release and a second light having a higher heat release and the switch and circuit board comprises a three position switch, wherein in a first position only the first light is illuminated, in a second position neither light is illuminated, and in a third position only the second light is illuminated.

6. The illuminated ear protector recited in claim 2, wherein the two light emitting diodes are identical, and the switch and circuit board comprise a three position switch wherein a first position is off, a second position is high intensity, and a third position is low intensity.

7. The illuminated ear protector recited in claim 2, further comprising a second reflector located within the rigid shell between the two light emitting diodes and the closed end such that light from the two light emitting diodes is directed towards the first reflector.

8. The illuminated ear protector recited in claim 2, wherein the two light emitting diodes each comprise internal reflectors which are adjusted to focus their light output to the first reflector.

9. The illuminated ear protector recited in claim 2, further comprising a sheet of translucent foam insulation shaped to fit on the closed end, whereby the light emitted from the closed end is diffused and sound penetration to the user's ear is reduced.

10. The illuminated ear protector recited in claim 2, further comprising a second foam sheet attached to the plate on a side opposite to the first reflector, whereby additional sound protection is provided.

11. The illuminated ear protector recited in claim 10, wherein the switch extends through the second foam sheet such that the two lights may be controlled from the open end.

* * * * *